United States Patent [19]

Rovesti et al.

[11] Patent Number: 5,607,674
[45] Date of Patent: Mar. 4, 1997

[54] USE OF TARCHONANTHUS CAMPHORATUS FOR REPELLING INSECTS AND ALLEVIATING EDEMA, CONGESTION AND IRRITATION OF THE SKIN

[75] Inventors: Guido Rovesti, Milan; Gabriele Segalla, Peschiera Del Garda; Pietro La Fratta, Milan; Michele G. Di Schiena, Cisliano, all of Italy

[73] Assignee: Gisquare Technologies B.V., Amsterdam, Netherlands

[21] Appl. No.: 428,175

[22] PCT Filed: Oct. 28, 1993

[86] PCT No.: PCT/EP93/02997

§ 371 Date: Jul. 10, 1995

§ 102(e) Date: Jul. 10, 1995

[87] PCT Pub. No.: WO94/09631

PCT Pub. Date: May 11, 1994

[30] Foreign Application Priority Data

Nov. 3, 1992 [GB] United Kingdom .................. 9222985

[51] Int. Cl.$^6$ .................................................. A61K 35/78
[52] U.S. Cl. .................................................. 424/195.1
[58] Field of Search .................................... 424/195.1

[56] References Cited

PUBLICATIONS

Martindale, The Extra Pharmacopoeia, 28 B ed. pp. 828–829 (1982).

Medical Botany, Published 1983 by John Wiley & Sons (New York) pp. 370–371.

Derwent Abstract #66–33730F, Wilmans, J. J. (1967).

*Primary Examiner*—Raymond Henley, III
*Attorney, Agent, or Firm*—Walter H. Schneider

[57] ABSTRACT

Utilization of the *Tarchanthus camphoratus* and its derivatives in formulations and compositions having insect repellant, anti-irritant, anti-edema, decongestant and soothing properties.

2 Claims, No Drawings

USE OF TARCHONANTHUS CAMPHORATUS FOR REPELLING INSECTS AND ALLEVIATING EDEMA, CONGESTION AND IRRITATION OF THE SKIN

This application is a 371 of PCT/EP93/02997 filed Oct. 28, 1993.

This invention relates to new uses of the *Tarchonanthus camphoratus*, utilization of its leaves, roots and branches either fresh, dried, soaked, extracted or in the form of essential oil.

The *Tarchonanthus camphoratus* is a shrub rearing in the wild in different African regions especially in the Rift uplands area. An experimental growing took also place in Italy (Canzonieri and Spica; Gazz. Chim. Ital. 1882, 227).

The shrub, mostly unknown by botanists, has different nares such as: Wild cotton, Sage wood, Wildesalie, Kamferhout, Kamferbos, Sieriehout, Vaalbos, Veld-vaalbos, Vaaibos, Sauto Mofahlana, Rolog e Thaalaping mohathla, well known in the local Swahili dialect with the name of "Leleshua", in the abissianian language "Ebok" and so on, or simply with the botanic name of *Tarchonanthus camphoratus*.

The *Tarchonanthus camphoratus* is a shrub reaching 2–4 m height; belonging to the Composite family, it has regular branches with velutinous white-greenish oval or lanceolate shaped leaves ranging from 4 to 13 cm lenght having a strong camphorated aromatic smell, whence its Linneana denomination.

This plant, with its wool-like, spike shaped flower heads is mentioned only in "The Medicinal and Poisonous Plants of Southern Africa" by John Mitchell Watt and Maria Gerdina Breyer-Brandwijk—Edimburgh, 1932 and in Paolo Rovesti's communication, presented at the XXIX International Congress of Industrial Chemistry in Paris in December 1956, "Ecological influences on the composition of the essential oils".

In the literature, mentioned herewith, various applications of this plant are known.

Engler mentions this species as used only for wood by the Usambara in Tanzania (Die Pflanzenwelt Afrikas—Tell B. Berlin, 1895, 357).

Braun tells the Masai (Tanzania) use it for wood-carving (Neil Gew. Pfl. Bd. XI, 2, 47).

Thonner is generally speaking about the plant precious medicinal properties using its leaves in fumigations and infusions (Die Blutenpflanzen Afrikas—Berlin 1908).

Dragerdorff tells that this species have the same therapeutic applications as *Salvia officinalis* (sage) (Die Heilpflanzen—Stuttgart 1898, 589).

Canzonieri and Spica made some studies about the supposed antipyretic properties/activities of *Tarchonantus Camphoratus* leaves (Gazz. Chim. Ital. 1882, 227).

Watt and Breyer tell the Ottentotti and other indigenous in the South Africa smoke the plant leaves using it as tobacco thanks to their slight narcosis forms. They are also used in fumigations against heathache, rheumatism and infusions (The medicinal and poisonous Plants of South Africa—Edimburg—1932, 189) against dyspepsia and toothache.—Pappe tells leaves contain some camphor but he gives no practical proof (Floras Capensis Medicae Prodromus—Capetown—1868, 178).

Pijper distilled an essential oil but he gave no details on its characteristics (De Volkggeneskunst in Transvaal—Leyden, 1919).

De Stefanis distilled, using some small branches with leaves sent from Eritrea to the Farmacognosia Laboratory of Turin University, an essence having a strong camphorated smell, with a yield of 0.1% and the following peculiarity: D 0,9152; i.a. 2,1; i.s. 11,8; i.s. after acethylene 85; I. Iodine 188,5; solubility 1:0.5 in alcohol at 95° (Boll. Inf. Econ. Minist. Colonie—Roma, 1924, n. 1).

Further details come from Rovesti's documentation which shows two plant distillations made in February (dried season) and in August (damp season) which took place in the Ethiopian tableland (XXIX International Congress of Industrial Chemistry, above cited).

|  | Yield % | $d_{15}°$ | $_D20$ | $n_D{}^{20}$ | I.S. | I.S. after acethyl. | Sol. |
|---|---|---|---|---|---|---|---|
| February essence | 0.108 | 0.9171 | −7°23' | 1.4681 | 31.73 | 149.33 | 1:3A 70° |
| August essence | 0.209 | 0.8968 | −2°15' | 1.4718 | 18.67 | 41.07 | 1:3A 90° |

It has now been found, and this is the subject of this invention, that some parts of the plant, in particular its leaves, fresh or dried and their derivatives, have some special insect repelling, insecticide, anti-edema, decongestant, anti-irritating and soothing properties that might be profitably used for therapeutic applications both for humans and animals.

The derivatives of this invention concern the *Tarchonanthus camphoratus* extracts obtained through an extraction as mentioned for example in the Italian Pharmacopeia.

Examples of extraction methods are: maceration, decoction, percolation and distillation.

There are then different derivatives such as the aqueous, the glycolic, the alcoholic, the hydroalcoholic, the soft and dried ones and, preferably, the essential oils.

One of the main goals of this invention is the use of the essential oil. According to the present invention, the application of this plant and of their derivatives concerns not only its insect repelling and insecticide action but also the treatment of irritations and inflammations caused by insect bites.

The efficacy of the *Tarchonanthus camphoratus* derivatives has been also found during some irritation and inflammatory conditions on cutis as for example eczema, ache, reddening, swelling and on genital and mouth mucosa.

The *Tarchonantus Camphoratus* essential oil obtained through a distillation in a steam flow, has been characterized using a GC/MS analysis, in this way 44 components were identified. Among these elements we find:

| | |
|---|---|
| Alpha Pinene | 15.40% |
| Camphene | 4.35% |
| Beta Pinene | 3.50% |
| Delta-2-Carene | 4.30% |
| Alpha Phellandrene | 1.60% |
| Limonene | 3.00% |
| Gamma Terpinene | 2.05% |
| Terpinolene | 1.35% |
| 1,8 Cineole | 12.10% |
| Fenchol | 14.40% |
| 1-Terpinen-4-ol | 2.30% |
| Alpha Terpineol | 4.50% |
| Fenchone | 0.85% |
| Trans Caryiophyllene | 1.15% |
| Bergamotene | 4.50% |
| Delta Cadinene | 1.40% |
| Alpha Curcumene | 1.70% |

The results of this research were presented at the Digne Congress in September 1992 (Ghizzoni, Rovesti, Colombo, Bottini).

Basing on a test of primary cutis irritation on human, it appears that the *Tarchonanthus camphoratus* oil spread as it is on 20 volunteers' healthy cutis in occlusive conditions, gave a medium irritation index of 0.4 after 15 minutes and of 0.35 after 24 hours the sample removal. Basing on the above mentioned parameter the product is then classified as non irritating.

The essential oil showed some surprising therapeutic anti-edema properties. The information about the applications of the essential oil, concerns in detail the edema status on lower limbs.

Another object of the present invention is the preparation and use of topical pharmaceutical compositions containing from 0.01 to 10% of *Tarchonanthus camphoratus* essential oil used as an active ingredient, alone or combined with other active materials.

The compositions can be made according to conventional methods as reported, for example, in the "Remington's Pharmaceutical Sciences Handbook" Mack Pub. New York U.S.A.

Some examples of pharmaceutical topical compositions are: solutions, suspensions, emulsions, ointments, creams, toothpastes in get form, sprays, prolonged release compositions such as transdermic plasters, and soaps.

One of the preferred embodiments of this invention is the preparation of insect-repelling and insecticide formulations containing from 0.01 to 10% of *Tarchonanthus camphoratus* essential oil as active ingredient, alone or with other similar components having the same activity.

Some examples of these preparations are: mosquito-fumigants, fumigants, vaporizing solutions, plates, sprays, stick, lotions, creams and gels.

The Tarchonanthus essential oil, put in different topical compositions having anti-edema, decongestant, anti-irritating, soothing activity, can be used in quantities ranging from 0.01% to 5%, preferably from 0.03% to 0.5%.

On the other side the Tarchonanthus essential oil, put in different topical formulations with insect-repelling and insecticide activity, can be used in quantities ranging from 0.03% to 7%, preferably from 0.05% to 3%.

In insect-repelling formulations, where the shrub or its essential oil are used at their natural state, the quantity must be 5% up to 95%. In this case it is advisable to use the plant during its balsamic period and immediately after its picking up; this, unfortunately, sets a limit to the Tharconanthus use at natural state, while no limit is fixed for its essential oil.

The activity of the essential oil, being part of this invention, has been tested in more than one pharmacological and clinical test.

1. Insect-repelling and insecticide activity.

A spray lotion containing 0.05% Tarchonanthus essential oil, in respect to the below mentioned formulation in example n. 1, was spreaded on 10 volunteers' skin who, during summer season evenings, laid in places with a high mosquitoes concentration.

It has been showed that among the 10 volunteers only 2 of them had mosquito-bites on two cutis areas.

A spray lotion containing 3% Tarchonanthus essential oil, in respect to the below mentioned formulation in example n. 3, was spread on 10 volunteers' skin who laid in places with a high mosquito concentration during summer evenings. It was shown that none of them had bites on the skin.

A *Tarchonantus camphoratus* essential oil alcoholic lotion, in respect to the below mentioned formulation in example n. 4, was used in a diffusor with absorbant tampon and put in a dimly airy room of about 60 mc infested with bothersome insects. Once the diffuser worked, an insecticide action started.

2. Anti-edema, decongestant, anti-irrirating and soothing activity.

An application of 0.1% Tarchonanthus essential oil gel, as per formulation in example 5, was spreaded on edematous legs, which gave immediate relief.

A gel containing 0.05% Tarchonatus essential oil, as per formulation in example 6, was put on female genitals with itching problems. That brought an immediate relief.

A gel containing 0.054% Tarchonanthus essential oil was used as per formulation in example 5, against bags under one's eyes. A rapid and surprising recovery took place.

A gel on 0.3% Tarchonantus essential oil basis, as mentioned in example n. 9, was used on a right ear as a remedy for a swelling due to a mosquito, or some other unidentified insect-bite. The problem was immediately solved. The same result was obtained after an application on different skin areas on 10 persons with various insect bites.

A gel on 0.05% Tarchonantus essential oil basis, as mentioned in example n. 6, was spread on 10 persons suffering from frequent erythema generally treated with a cortisone cream. It was found that all the subject recovered rapidly and both the painful and itching sensations disappeared.

An alcoholic solution containing 0.1% Tarchonantus essential oil, see example n. 12, was put, by means of a tampon, on a pimply skin full with acne on 10 patients. In all the above mentioned situations the problem was totally solved. The same preparation was put on recent pimples that disappeared 24 hours later.

A gel with 0.1% Tarconanthus essential oil was used, as per example n. 7, on 5 subjects' face and neck skin and on armpits and legs suffering from irritation after shaving and depilation treatments. They both declared a relief and freshness sensation.

A fluid emulsion containing 0.1% Tarchonanthus essential oil, as per example n.13, was spreaded on genital and anal areas on 2 aged people and on 3 new borns, suffering from itching conditions due to napkins use. All the cases were solved rapidly.

A fluid emulsion on 0.1% Tarchonantus essential oil, see example 14, was spreaded on bedsores on 3 patients. In all these cases the recovery was rapid, the edema and the irritation improved.

A gel containing 0.5% Tarchonantus essential oil, as per example n. 6, was spreaded on 7 subject with itching problems on the anal area due to hemorrhoids and rhagades. They recovered rapidly declaring a freshness and relief sensation.

A mouthwash with 20% infusion, worked at cold state, obtained from Tarchonantus grinded fresh leaves, as in example n.16, was used on 5 patients having irritated gums. In these cases a constant and periodic application brought a relief with a consequent decongestion of gums together with a freshness sensation and a good smelling breath.

A toothpaste with 0.2% Tarchonanthus essential oil, as mentioned in example n. 15, was used in 5 cases suffering from slightly irritated gums. A constant and periodic use of the formulation was of help in the gums decongestion. A freshness sensation and a good smelling breath was also noticed.

An alcoholic gel containing 1% Tarchonanthus essential oil, as per example n. 10, was used on legs suffering from phlebitis. A constant and periodic use was of help to solve the problem.

An alcoholic gel containing 0.8% Tarchonantus essential oil as per example n. 11, was spreaded on haematoma on 3 subjects. In both cases, a constant and periodic use, was of help to improve the edema problem.

The following examples further illustrate the invention. For sake of brevity, the essential oil is called E.O.

EXAMPLE N. 1

Insecticide spay lotion

| | |
|---|---|
| PEG 40 Hydrogenated Castor Oil | 0.2% |
| Glycerine | 3% |
| Tarchonanthus camphoratus E.O. | 0.05% |
| Preservatives (antibacterial/antimould) | q.s. |
| Demineralized water | q.s. to 100% |

EXAMPLE N. 2

Insecticide spray lotion

| | |
|---|---|
| PEG 40 Hydrogenated Castor oil | 4% |
| Glycerine | 3% |
| Tarchonanthus camphoratus E.O. | 1% |
| Preservatives (antibacterial/antimould) | q.s. |
| Demineralized water | q.s. to 100% |

EXAMPLE N. 3

Insecticide spray lotion

| | |
|---|---|
| Peg 40 Hydrogenated Castor Oil | 12% |
| Glycerine | 3% |
| Tarchonanthus camphoratus E.O. | 3% |
| Preservatives (antibacterial/antimould) | q.s. |
| Demineralized water | q.s. to 100% |

EXAMPLE N. 4

Insecticide alcoholic solutions for environmental purposes

| | |
|---|---|
| Methylated alcohol type A | 42% |
| Tarchonanthus camphoratus E.O. | 5% |
| Sorbitan monoleate 20 (OE) | 13% |
| Demineralized water | q.s. to 100% |

EXAMPLE N. 5

Anti-edema gel

| | |
|---|---|
| Carboxyvinyl polymer (Carbomer 940) | 0.76% |
| Glycerine | 3% |
| Sorbitan 20 (OE) monolaurate | 0.4% |
| Tarchonanthus camphoratus E.O. | 0.1% |
| Preservatives (antibacterial/antimould) | q.s. |
| Triethanolamine | 0.5% |
| Demineralized water | q.s. to 100% |

EXAMPLE N. 6

Anti-irritating, soothing gel

| | |
|---|---|
| Carboxyvinyl polymer (Carbomer 940) | 0.76% |
| Glycerine | 3% |
| Sorbitan 20 (OE) monolaurate | 0.2% |
| Tarchonanthus camphoratus E.O. | 0.05% |
| Preservatives (antibacterial/antimould) | q.s. |
| Triethanolamine | 0.5% |
| Demineralized water | q.s. to 100% |

EXAMPLE N. 7

Anti-irritating gel pre/after shave/depilation

| | |
|---|---|
| Carboxyvinyl polymer (Carbomer 940) | 0.5% |
| Glycerine | 3% |
| Sorbitan 20 (E.O:) monolaurate | 0.2% |
| Tarchonanthus camphoratus E.O. | 0.04% |
| Preservatives (antibacterial/antimould) | q.s. |
| Triethanolamine | 0.3% |
| Demineralized water | q.s. to 100% |

EXAMPLE N. 8

After sun gel

| | |
|---|---|
| Carboxyvinyl polymer (Carbomer 940) | 0.76% |
| Glycerine | 3% |
| Sorbitan 20 (OE) monolaurate | 0.4% |
| Tarchonanthus camphoratus E.O. | 0.1% |
| Preservatives (antibacterial/antimould) | q.s. |
| Triethanolamine | 0.5% |
| Demineralized water | q.s. to 100% |

EXAMPLE N. 9

Anti-edema gel

| | |
|---|---|
| Carboxyvinyl Polymer (Carbomer 940) | 0.70% |
| Glycerine | 3% |
| Sorbitan 20 (OE) monolaurate | 1.2% |
| Tarchonanthus camphoratus E.O. | 0.3% |
| Preservatives (antibacterial/antimould) | q.s. |
| Triethanolamine | 0.45% |
| Demineralized water | q.s. to 100% |

EXAMPLE N. 10

Anti-edema alcoholic gel

| | |
|---|---|
| Carboxyvinyl polymer (Carbomer 940) | 0.5% |
| Alcohol type D | 40% |
| Glycerine | 5% |
| Peg 40 Hydrogenated Castor Oil | 3% |
| Tarchonanthus camphoratus E.O. | 1% |
| Preservatives (antibacterial/antimould) | q.s. |
| Triethanolamine | 0.3% |
| Demineralized water | q.s. to 100% |

EXAMPLE N. 11

Soothing/refreshing alcoholic gel

| | |
|---|---|
| Carboxyvinyl polymer (Carbomer 940) | 0.5% |
| Alcohol type D | 40% |
| Glycerine | 5% |
| Peg 40 Hydrogenated Castor Oil | 2.5% |
| Tarchonanthus camphoratus E.O. | 0.8% |
| Preservatives (antibacterial/antimould) | q.s. |
| Triethanolamine | 0.3% |
| Demineralized water | q.s. to 100% |

EXAMPLE N. 12

Alcoholic solution for pimply skins

| | | |
|---|---|---|
| Alcohol type C | | 40% |
| Glycerine | | 2% |
| Sorbitan 20 (OE) monolaurate | | 2% |
| Tarchonanthus camphoratus E.O. | | 0.1% |
| Lavender e.o. | | 0.4% |
| Demineralized water | q.s. | to 100% |

EXAMPLE N. 13

Anti-irritating fluid emulsion

| | | |
|---|---|---|
| Carboxyvinyl polymer (Carbomer 940) | | 0.30% |
| Glycerine | | 6% |
| Tarchonanthus camphoratus E.O. | | 0.1% |
| Triethanolamine | | 0.2% |
| Acethylated Lanoline | | 1% |
| Dimethylpolyxyloxane | | 1% |
| Myristil lactate | | 2% |
| Decyle oleate | | 2% |
| Preservatives (antibacterial/antimould) | q.s. | |
| Demineralized water | q.s. | to 100% |

EXAMPLE N. 14

Anti-irritating/decongestant fluid emulsion

| | | |
|---|---|---|
| Carboxyvinyl plymer (Carbomer 940) | | 0.30% |
| Glycerine | | 6% |
| Tarchonanthus camphoratus E.O. | | 0.1% |
| Allantoine | | 1% |
| Tocopheryl acetate | | 0.5% |
| Triethanolamine | | 0.2% |
| Acethylated lanoline | | 1% |
| Dimethylpolyxiloxane | | 1% |
| Myristil lactate | | 2% |
| Decyl oleate | | 2% |
| Preservatives (antibacterial/antimould) | q.s. | |
| Demineralized water | q.s. | to 100% |

EXAMPLE N. 15

Gum toothpaste

| | | |
|---|---|---|
| Potassium sorbate | | 0.2% |
| Glycerine | | 11% |
| Sorbitan 20 (OE) monolaurate | | 0.8% |
| Tarchonanthus camphoratus E.O. | | 0.2% |
| Carboxyvinyl cellulose medium density | | 1.5% |
| Dicalcium phosphate di-hydrate | | 48% |
| Sorbitol 70% | | 11% |
| Sodium laurilether sulphate | | 2% |
| Acesulfame Hoechst (sweetener) | | 0.2% |
| Preservatives (antibacterial/antimould) | q.s. | |
| Demineralized water | q.s. | to 100% |

EXAMPLE N. 16

Idroalcoholic mouthwash

| | | |
|---|---|---|
| Alcohol type E | | 15% |
| Glycerine | | 4% |
| Glycyrrhizinate ammonium | | 0.1% |
| Tarchonanthus infusion at cold state grinded fresh leaves at slow stirring for 7 days in demin. water preserved | | 20% |
| Demineralized water | q.s. | to 100% |

EXAMPLE N. 17

Mosquito fumigant

A convenient quantity of dried leaves, belonging to a plant picked up by no more than 30 days, was grounded small.

30% of it was mixed up with arabic gum (10%), pit-coal (50%) potassium nitrate (10%), worked in water, spiral shaped and dried in a heater at 35° C. for 24 hrs.

The same examples can be formulated with extracts and soaked in the proper concentrations.

We claim:

1. A method for repelling insects, and alleviating edema, congestion and skin irritation symptoms which comprises applying to the cutis of an individual a pharmaceutical composition comprising as the principal active ingredient from 0.01–10% of the extract of *Tarchonathus camphoratus* together with a pharmaceutically acceptable carrier.

2. A method for alleviating edema, congestion and skin irritation symptoms which comprises applying to the cutis of an individual a pharmaceutical composition comprising as the principal active ingredient from 0.03–0.5% of the extract of *Tarchonathus camphoratus* together with a pharmaceutically acceptable carrier.

* * * * *

(12) EX PARTE REEXAMINATION CERTIFICATE (5138th)
United States Patent
Rovesti et al.

(10) Number: US 5,607,674 C1
(45) Certificate Issued: Jul. 12, 2005

(54) **USE OF *TARCHONATHUS CAMPHORATUS* FOR REPELLING INSECTS AND ALLEVIATING EDEMA, CONGESTION AND IRRITATION OF THE SKIN**

(75) Inventors: Guido Rovesti, Milan (IT); Gabriele Segalla, Peschiera Del Garda (IT); Pietro La Fratta, Milan (IT); Michele G. Di Schiena, Cisliano (IT)

(73) Assignee: Gisquare Technologies, B.V., Amsterdam (NL)

Reexamination Request:
No. 90/006,538, Feb. 5, 2003

Reexamination Certificate for:
Patent No.: 5,607,674
Issued: Mar. 4, 1997
Appl. No.: 08/428,175
Filed: Jul. 10, 1995

(22) PCT Filed: Oct. 28, 1993

(86) PCT No.: PCT/EP93/02997
§ 371 (c)(1),
(2), (4) Date: Jul. 10, 1995

(87) PCT Pub. No.: WO94/09631
PCT Pub. Date: May 11, 1994

(30) Foreign Application Priority Data
Nov. 3, 1992 (GB) .............................................. 9222985

(51) Int. Cl.$^7$ ............................................... A61K 35/78
(52) U.S. Cl. ...................................................... 424/764
(58) Field of Search .......................... 424/764, DIG. 10; 514/853, 870, 886, 887, 919

(56) References Cited

PUBLICATIONS

Watt, John M. et al. The Medicinal and Poisonous Plants of Southern and Eastern Africa. E & S Livingstone Ltd., Edinburgh, 1962, pp. 294–295.*

Roberts, M. Indigenous Healing Plants. Southern Book Publishers, 1990, pp. 219–220.*

Webster's New World Dictionary, Simon & Schuster, Inc., New York, Third College Edition, 1988, p. 243.*

John Mitchell Watt and Maria Gerdina Breyer–Brandwijk; The Medicinal and Poisonous Plants of Southern and Eastern Africa; E. & S. Livingstone Ltd., Edinburgh and London, 1962; pp. 294–295.

Margaret Roberts; Indigenous Healing Plants; Southern Book Publishers, 1990. ISBN No. 1–86812–317–0; pp. 219–220.

* cited by examiner

*Primary Examiner*—John Pak

(57) ABSTRACT

Utilization of the *Tarchanthus camphoratus* and its derivatives in formulations and compositions having insect repellant, anti-irritant, anti-edema, decongestant and soothing properties.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1 and 2 are cancelled.

* * * * *